United States Patent [19]

Harms et al.

[11] Patent Number: 5,441,889
[45] Date of Patent: Aug. 15, 1995

[54] MHC EUKARYOTIC PROMOTER

[75] Inventors: Jerome S. Harms, Madison; Gary A. Splitter, Brooklyn, both of Wis.

[73] Assignee: Wisconsin Alumni Research Foundation, Madison, Wis.

[21] Appl. No.: 180,187

[22] Filed: Jan. 11, 1994

[51] Int. Cl.$^6$ ..................... C12N 15/85; C12N 15/11
[52] U.S. Cl. ................... 435/320.1; 536/24.1
[58] Field of Search .................... 536/24.1; 435/320.1

[56] References Cited

PUBLICATIONS

Ovnic et al. 1991, Genomics 11:956–967.
Koller et al. 1985, J. of Immunology, 134(4):2727–2733.
T. Garber, et al., "Sequence and evolution of cattle MHC class I cDNAS: concerted evolution has not taken place in cattle", 38 *Immunogenetics*, 11–20 (1993).
A. Bensaid, et al., "Identification of expressed bovine class I MHC genes at two loci and demonstration of physical linkage", 33 *Immunogenetics*, 247–254 (1991).
P. Ennis, et al., "Molecular Cloning of Bovine Class I MHC cDNA", 141 *J. Immunol*, 642–651 (1988).
P. Brown, et al., "Cloning and characterization of a BoLA class I cDNA clone", 29 *Immunogenetics*, 58–60 (1989).
R. Hakem, et al., "Differential Regulation of HLA–A3 and HLA–B7 MHC Class I Genes by IFN . . . ", 147 *J. Immunol.*, 2384–2390 (1991).
A. Kimura, et al., "Detailed Analysis of the Mouse H–2K$^b$ Promoter . . . ", 44 *Cell*. 261–272 (1986).
J. Weissman, et al., "A Complex Regulatory DNA Element Associated with a MHC Class I Gene . . . ", 11 *Mol. Cell. Biol.*, 4217–4227 (1991).
M. Kay, et al., "In Vivo Gene Therapy of Hemophilia B . . . ", 262 *Science*. 117–119 (1993).
J. Marx, "A First Step Toward Gene Therapy for Hemophilia B?", 262 *Science*, 29–30 (1993).
M. Manthorpe, et al., "Gene Therapy by Intramuscular Injection of Plasmid DNA . . . ", 4 *Human Gene Therapy*, 419–431 (1993).

*Primary Examiner*—Richard A. Schwartz
*Assistant Examiner*—Nancy T. Vogel
*Attorney, Agent, or Firm*—Quarles & Brady

[57] ABSTRACT

A promoter/enhancer for a bovine MHC class I gene is incorporated in recombinant nucleotide sequences and vectors. In one form, the promoter/enhancer may be linked to a foreign gene for permitting expression of the foreign gene in a wide range of mammalian host cells.

2 Claims, 3 Drawing Sheets

5,441,889

MHC EUKARYOTIC PROMOTER

This invention was made with United States Government support awarded by the U.S. Department of Agriculture (USDA), Grant Nos. 88-CRSR-37265-3730 and 90-37265-5703. The United States Government has certain rights in this invention.

FIELD OF THE INVENTION

The present invention relates generally to the isolation and uses of a promoter/enhancer for a bovine major histocompatibility complex (MHC) class I gene.

BACKGROUND OF THE INVENTION

A promoter is a specific DNA sequence that signals where RNA synthesis should begin. Most genes in higher eukaryotes are regulated by the combination of a nearby upstream promoter element plus an enhancer element. The enhancer typically works by providing binding sites for gene regulatory proteins that increase transcription.

DNA vectors (e.g. plasmids; viruses) can be modified to include a gene for a foreign protein. Some of these recombinant vectors contain a promoter/enhancer necessary for expression of the gene upstream from what is known as a cloning site (e.g. a rare or unique restriction enzyme site where a foreign gene of interest can be inserted). The recombinant expression vectors can then be transfected into mammalian cells or tissues where the foreign gene is to be expressed.

Such expression vectors are of great value for purposes such as transgenics and gene therapy. In transgenics, recombinant genes are transferred into animals at an early, embryonal stage of development where the gene inserts into the genome and is passed on to all cells of the animal. Expression of the gene then supplements defects, adds desirable traits, or helps in understanding development.

Gene therapy is slightly different. Current strategy for gene therapy is first to identify the defective gene, then to supplement the defective tissues with the functional gene. Transgenics and gene therapy are merely two examples of a broad range of uses for expression vectors in biology and medicine. Expression vectors also have many in vitro uses, such as permitting production of large amounts of a protein of interest.

Viral recombinant promoter elements are currently the most widely used. Typically they are from pathogenic viruses such as Epstein Barr Virus (EBV), Human Cytomegalovirus (CMV), Rous Sarcoma Virus (RSV) and Simian Virus 40 (SV40). See M. Manthorpe, et al., 4 *Human Gene Therapy* 419–431 (1993); J. Marx, 262 *Science* 29–30 (1993); and M. Kay, et al., 262 *Science* 117–119 (1993). These references and all other references cited herein are hereby incorporated by reference as if fully set forth herein. The use of viral promoters has lead to safety concerns, and in some cases certain viral promoters have turned off after a time when in a eukaryotic host. Also, some viral promoters have over promoted at first (and thus dominated the cell).

The very few mammalian promoters in use in recombinant systems have been comparatively weak in their ability to initiate transcription, and/or are restricted to a limited set of tissues, and/or are from hosts that are not desirable for various purposes. For example, a human promoter inserted into a human cell might interact in undesirable ways with other cell functions. Also, promoters and enhancers that are too different from human cell promoters might not be able to work as efficiently with certain host cells. Some known MHC promoters are reported in J. Weissman, et al., 11 *Molecular and Cellular Biology* 4217–4227 (1991) (pig); A. Kimura, et al., 44 *Cell* 261–272 (1986) (mouse); and R. Hakem, et al., 147 *Journal of Immunology* 2384–2390 (1991) (human).

Accordingly, there is a need for an improved mammalian promoter/enhancer that when part of a recombinant sequence initiates high levels of transcription in a wide range of mammalian cell types.

SUMMARY OF THE INVENTION

One aspect of the invention provides a recombinant nucleotide sequence having a first nucleotide sequence encoding a promoter for a bovine MHC class I gene where the promoter is linked to a non-bovine gene. The promoter is positioned so as to be able to regulate the non-bovine gene (e.g. regulating transcription). Preferably, the first nucleotide sequence also has a bovine MHC class I gene enhancer sequence.

In another aspect, the invention provides a recombinant vector having a nucleotide sequence encoding a promoter for a bovine MHC class I gene; a vector backbone; and a cloning site positioned so as to be suitable to receive a foreign gene so that the foreign gene can be expressed under the regulation of the bovine promoter. Preferably, the recombinant nucleotide sequence also has a bovine MHC class I gene enhancer sequence. A plasmid or virus can form a "vector backbone".

An especially preferred construct is where the nucleotide sequence comprises substantially SEQ ID NO: 1 bases 1–96.

In addition to the uses described above for recombinant vectors generally, the present invention has many potential other applications. As merely an example, one research use of the present invention might be to control an antibiotic resistant gene or a marker for selection or feedback purposes. A more commercial use of the concept is to produce large amounts of a desired antigen in vivo for vaccine purpose.

One particular advantage of the promoter/enhancer of the present invention is that it is susceptible of being regulated. For example, our experiments have shown that expression of the protein of interest can be upregulated with cytokines such as tumor necrosis factor. We believe that it can also be down regulated with the c-myc oncogene.

Another advantage is that the SEQ ID NO: 1 sequence is not cut by most restriction enzymes that are now widely used for genetic manipulation. Therefore, it would be suitable for use in a vector kit system, where the gene for the protein of interest is inserted into the vector.

An object of the present invention therefore is providing vectors and sequences of the above kind, where expression is highly efficient in a wide range of mammalian tissues. These and still other objects and advantages of the present invention will be apparent from the description below.

DESCRIPTION OF THE PREFERRED EMBODIMENTS

Overview

We have isolated and incorporated into vectors a promoter/enhancer for a bovine major histocompatibility complex (MHC) class I gene. It is in SEQ ID NO: 1. SEQ ID NO: 1 consists of all necessary elements for eukaryotic transcription initiation—the promoter (1–27), the enhancerA/IRS region (28–96), the CAAT box (187–190), the TATA box (214–219), and a transcription initiation site. We call this sequence promoter "BL3-6". For a general discussion of bovine MHC class I genes (as distinguished from their promoters) see T. Garber, et al., 38 *Immunogenetics* 11–20 (1993); A. Bensaid, et al., 33 *Immunogenetics* 247–254 (1991); P. Ennis, et al., 141 *J. Immunol.* 642–651 (1988); and P. Brown, et al., 29 *Immunogenetics* 58–60 (1989).

Figure 1:
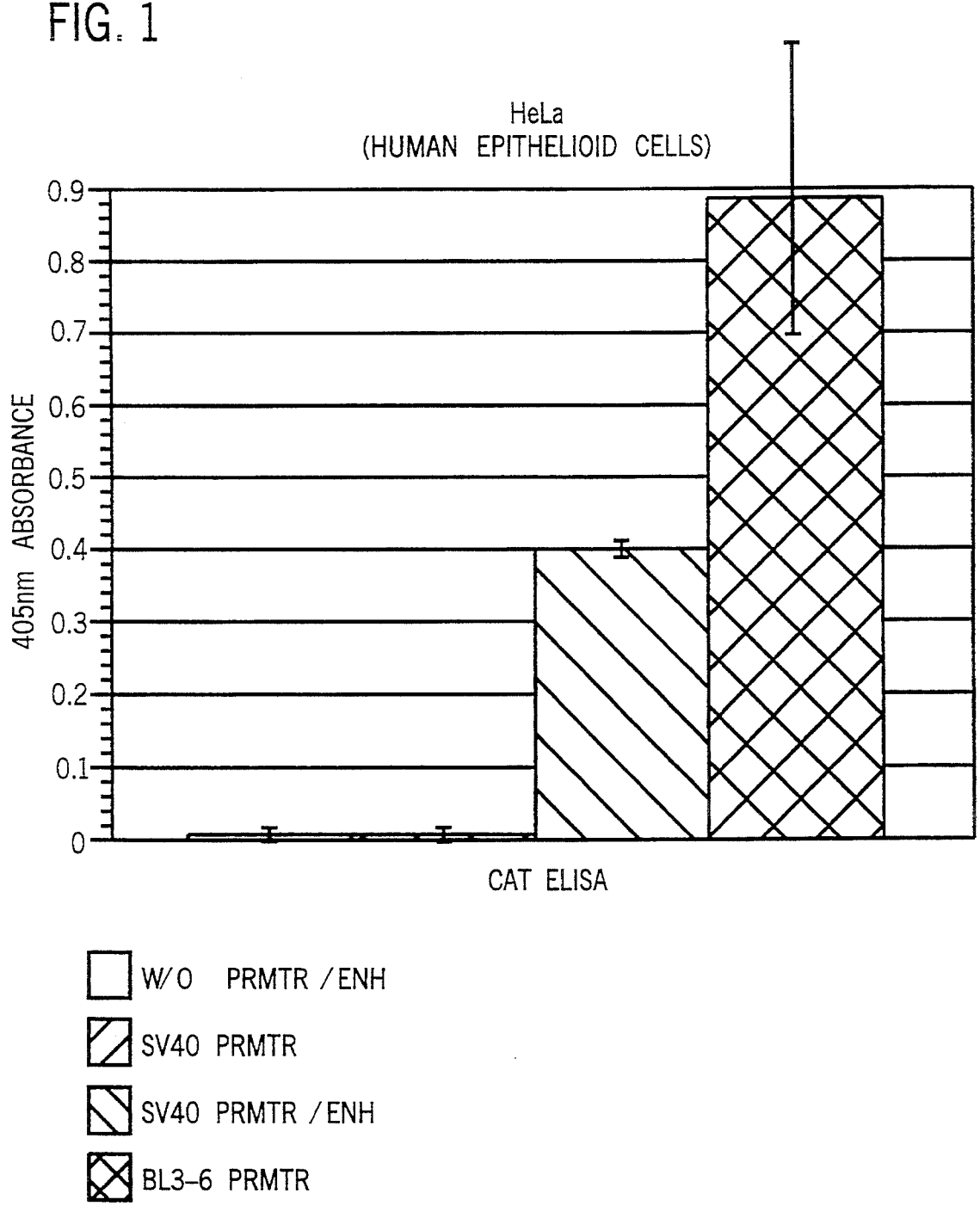
FIG. 1 is a bar graph comparing the expression levels in human epitheliod cells for a widely used viral promoter with a promoter of the present invention.
Figure 2:
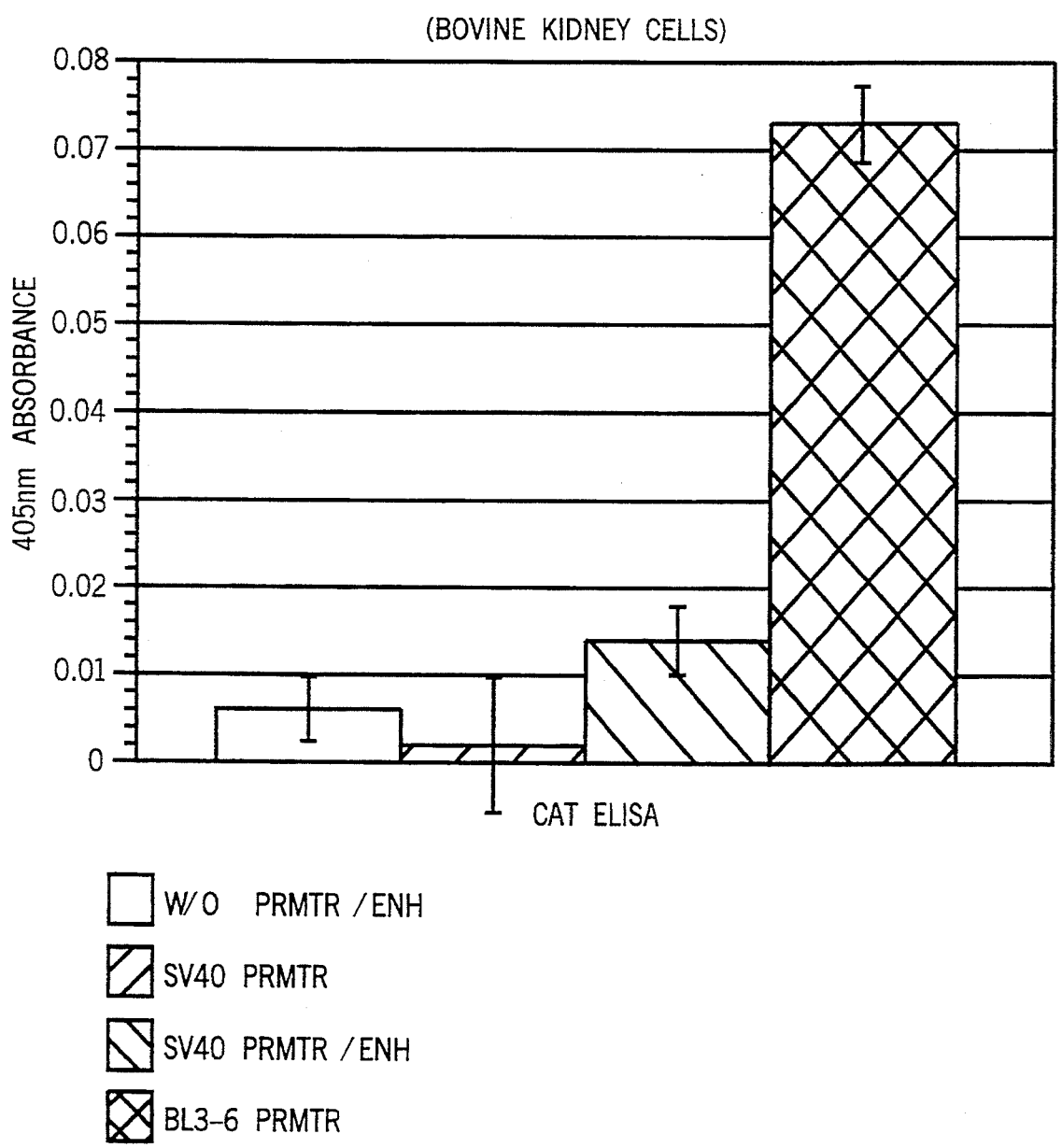
FIG. 2 is a comparison similar to FIG. 1, but in bovine kidney cells.
Figure 3:
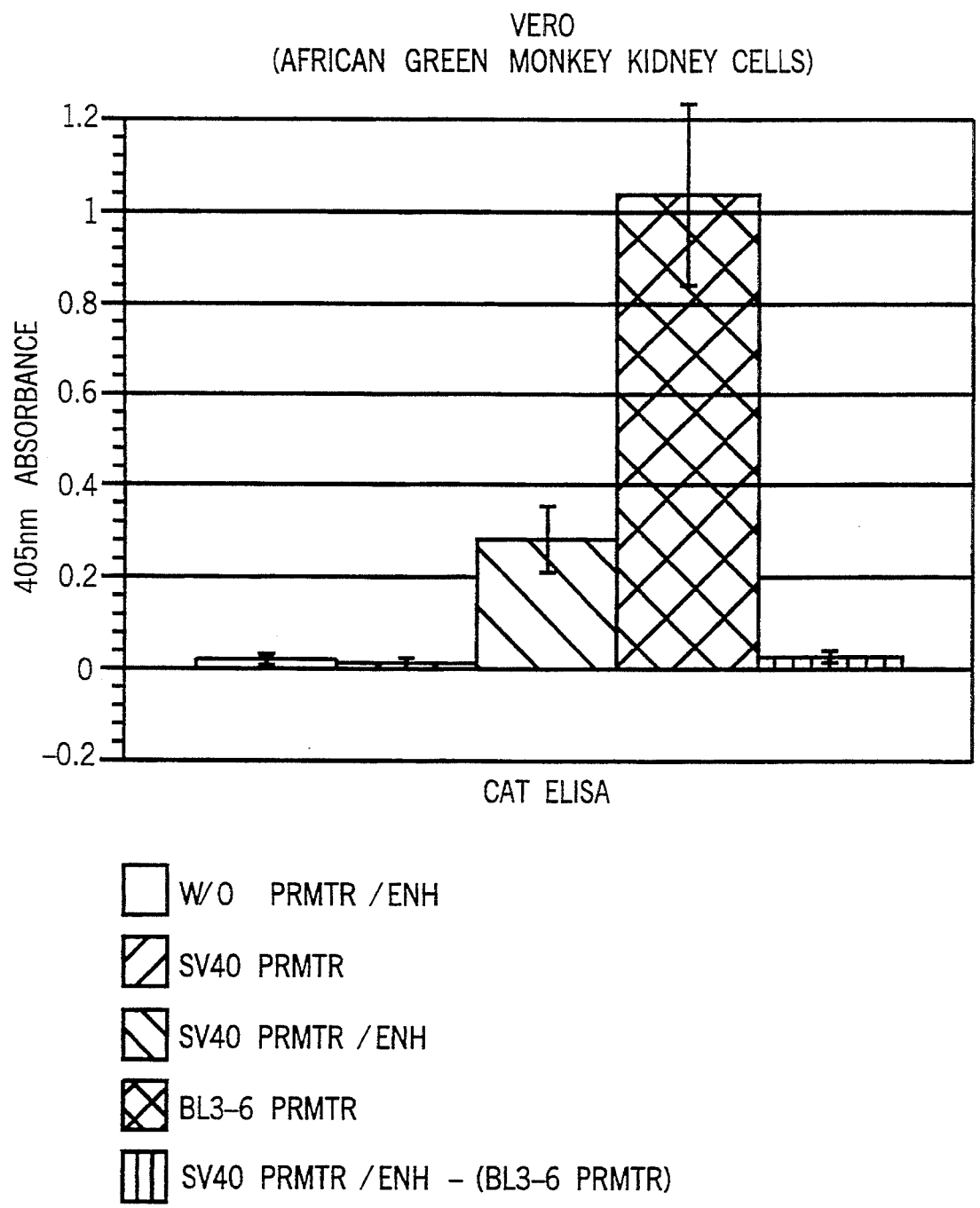
FIG. 3 is a comparison similar to FIG. 2, but in monkey cells.

To confirm its function and compare its strength, the BL3-6prmtr was linked to a chloramphenicol acetyltransferase (CAT) reporter gene at the 3' end of SEQ ID NO: 3, then transfected into cell lines of different species. The commonly used, commercially available SV40 promoter/enhancer CAT vector (Promega Corp.) was also transfected into the same cell lines and promoter activity of the two was compared through CAT enzyme immunoassays (see FIGS. 1–3). While four cell types were successfully tried (human, bovine, monkey, and dog) it is believed that the BL3-6prmtr should be useful in mammals in general including without limitation a wide range of primates. Within an animal, the system should regulate expression of a wide range of foreign genes of interest (e.g. proteins of various types) in a wide range of tissue types. In this regard, MHC class I protein is expressed in a wide range of tissues.

The present invention also takes advantage of the fact that cytokine stimulation, viral infection, and tumor progression can all cause MHC class I expression modulation (thereby affecting immune response). The mechanism for modulation is at the level of transcription initiation. As such, the present system has been shown to be susceptible to being up regulated, and should be susceptible to being down regulated.

Isolation of Promoter/Enhancer

We developed a unique PCR approach to isolate the sequence. One primer was developed based on part of a bovine MHC gene and another based on a human gene. Moreover, there were other serious difficulties that had to be overcome in setting hybridization and other PCR conditions. Overly stringent hybridization conditions would yield no product. If stringency was reduced too low, multiple undesired binding sites could appear. Also, too large a primer could lead to primer interference.

Bovine genomic DNA, isolated from the bovine B-lymphosarcoma cell line, BL3, was amplified using mixed primer pairs we specially designed from sequences of human HLA-A2 for the 5' end (SEQ ID NO: 2) and bovine BL3-6 for the 3' end (SEQ ID NO: 3). PCR was carried out on a 100 μl final reaction mix consisting of 2.5 mMMgCl₂, 200μM each of dATP, dCTP, dGTP, and dTTP, 0.5μM of each primer, 1 μg of DNA, and 2.5 Units of Stoffel fragment, Amplitaq DNA Polymerase in 1.25X buffer (Perkin Elmer Cetus, Norwalk, Conn.) using a DNA Thermal Cycler (Perkin Elmer Cetus). The thermal cycle protocol was: 94° C., 1 min, 1 cycl; 94° C., 1 min, 55° C., 1 min, 72° C., 1 min, 30 cycles; 72° C., 10 min, 1 cycle. The entire reaction was run on a 4% low melting point agarose gel and a DNA band of approximately 330 bp was excised and purified using Geneclean (BIO 101, Inc., LaJolla, Calif.).

Subcloning and Sequencing

The PCR fragment was subcloned into the SmaI site of pGem-3Z (Promega Corp., Madison, Wis.) and sequenced. Dideoxy sequencing was performed using a Sequenase 2.0 kit (USB, Cleveland, Ohio) and T7 and Sp6 Sequencing primers (Promega). Separation was on a Sequagel-6, 6% sequencing gel (National Diagnostics, Atlanta, Ga.). The resultant bovine MHC class I promoter clone was named pBL3-6prmtr. The BL3-prmtr was subcloned into a chloramphenicol acetyltransferase (CAT) reporter gene vector. Briefly, a TaqI fragment of pBL3-6prmtr consisting of the entire promoter fragment plus 30 bp of pGem-3Z was subcloned into the AccI site of pCAT Basic (Promega). Clones were checked for proper orientation to the CAT gene by restriction digests and the resulting expression vector was named pCAT BL3-6prmtr. BL3-6prmtr was also sub-cloned into a luciferase expression vector using a Sau 3A1 fragment of pBL3-6prmtr and BglII site of pGL Basic (Promega). The resulting luciferase expression vector was named, pGL BL3-6prmtr. All plasmid DNA was purified using Qiagen columns (Qiagen Inc., Chatsworth, Calif.).

Transient Transfections and Analysis

The reporter gene vector pCAT BL3-6prmtr along with control vectors pCAT Basic and pCAT Control (Promega) were transiently transfected into four different cell lines. The cell lines MDBK (normal bovine kidney, ATCC CRL 6071), HeLa (human epithelioid carcinoma, ATCC CCL2), Vero (African Green Monkey kidney, ATCC CCL81), and D-17 (canine primary osteogenic sarcoma, ATCC CCL 183) were transiently transfected using LipofectAMINE liposome reagent (GIBCO BRL, Gaithersburg, Md.) following the manufacturer's recommended protocol. Twenty-four to forty-eight hours after transfection, cell extracts were prepared and analyzed for promoter activity using a CAT ELISA system (Boehringer Mannheim Corp., Indianapolis, Ind.). Absorbance readings at 405nm were taken on a Microplate Autoreader (BIO-TEK Instruments, Inc., Winooski, Vt.).

Similarly, pGL BL3-6prmtr along with control vectors pGL Basic and pGL Control (Promega) were transfected into the human colorectal cell lines COLO 320 HSR (ATCC CCL 220.1) and SW837 (ATCC CCL 235). Cell extracts were prepared and analyzed using a luciferase assay system (Promega) measured on a Monolight 2010 luminometer (Analytical Luminescence Laboratory, San Diego, Calif.).

Results

Polymerase chain reaction (PCR) was used to isolate a cattle MHC class I promoter. Although no BoLA promoter sequence was available, two full length, apparently functional, MHC class I cDNA clones had perviously been isolated from a BL3 cDNA library. P. Ennis, et al., 141 J. *Immunol.* 642–651 (1988). A leader peptide DNA sequence of one of these clones, BL3-6, was therefore chosen as the 3' end primer for the PCR. No 5' primer bovine model was available.

In accordance with our invention, a sequence from a human HLA-A2 promoter was chosen for the degenerate 5' end primer. Using this semi-degenerate primer pair, and unique hybridization and reaction conditions, a roughly 330 bp fragment was isolated, subcloned, and sequenced. The sequence revealed the fragment to be a bovine MHC class I promoter we have designated as BL3-6prmtr (SEQ ID NO: 1).

Upon further checking, we have learned that the human HLA-A1 gene had only relatively weak homology to the BL3-6prmtr. HLA-B and -C sequences had even lower homology.

Industrial Applicability

As an example of industrial applicability, we sought to replace the CMV promoter/enhancer in the mammalian expression vector, pcDNA3 (Invitrogen Corp., San Diego, Calif.) with our BL3-6prmtr. The CMV promoter was removed from pcDNA3 by restriction digesting with Nru I and Hind III. The overhanging ends of the remaining vector backbone were blunt ended with T4 Polymerase and then dephosphorylated using calf intestinal alkaline phosphatase (CIAP). Since most genes to be subcloned contain an ATG translation start site, BL3-6prmtr was prepared for insertion into the now promoterless pcDNA3 vector by eliminating the ATG translation start site using Nla III, then blunt ending with T4 polymerase. However, BL3-6prmtr has the advantage of being able to be used essentially intact for creation of an expression vector for production of chimeric or fusion proteins. The prepared BL3-6prmtr was then ligated into the pcDNA3 vector backbone and the resultant clone, pcBL3-6, was checked for proper orientation by sequencing.

We then subcloned a *Brucella abortus* 12 kD and luciferase genes into pcBL3-6. The mammalian expression vector pcBL3-6 was modified by restriction enzyme digesting in the multiple clone site (MCS) with the blunt end cutter EcoR V and then dephosphorylating. The 12 kD gene was isolated from its pFLAG vector using Xho I and Xba I and blunt ending with T4 polymerase. The vector pcBL3-6 and insert 12 kD gene were then ligated and correct orientation of the resultant clone checked by restriction digests.

For subcloning of luciferase, pcBL3-6 was digested with Not I and Xho I and then dephosphorylated. The luciferase gene was prepared from pGem-luc (Promega Corp., Madison, Wis.) using Not I and Xho I. Vector and insert were ligated and clones checked for orientation by restriction digests. The same protocol was used for subcloning the 12 kD and luciferase genes into pcDNA3 for promoter comparison purposes.

The commonly used mastoma P815 and B-lymphoma A20.J cell lines were transfected with the pcBL3-6/12kD construct by the cationic lipid method and neomycin selected for stable integration of the gene. Northern blots confirmed high expression of the 12kD gene and cells were used in cytotoxicity assays that showed the immunological importance of the 12 kD gene product. *Brucella abortus* causes undesired abortions in cattle. We believe that protein expressed in quantity through use of our promoter will raise a cellular response in cattle, and thus perhaps be a vaccine.

Although the present invention has been described with reference to certain preferred embodiments, other versions are possible. For example, other bovine MHC Class I promoter/enhancers can now be obtained using portions of the present sequence as a hybridization probe (or for PCR primer guidance). Also, numerous other foreign genes of interest can be used in place of the reporter gene test model, and recovered in quantity. Thus, the invention is not to be limited to just the specific embodiments described. The claims should be looked to to judge the full scope of the invention.

We claim:
1. A recombinant nucleotide sequence, comprising:
   a nucleotide sequence (SEQ ID NO: 1, positions 1-27) or a portion thereof which retains promoter function encoding a promoter for a bovine MHC class I gene where said promoter is linked to a non-bovine gene and positioned so as to be able to regulate the transcription of the non-bovine gene.
2. A recombinant vector comprising:
   a nucleotide sequence (SEQ ID NO: 1, positions 1-27) or a portion thereof which retains promoter function encoding a promoter for a bovine MHC class I gene;
   a vector backbone; and
   a cloning site positioned so as to be suitable to receive a foreign gene so that the foreign gene can be expressed under the regulation of the bovine promoter.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 332 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

```
AGGCGTTGGC TCTCAGGGTC TCAGGGTCAA GGGCTGTGTC TGGGGCTGGG ACGCTCTATA    60
TTGGGCATTC CCTGTCTCCC CAAGTTTCAC TTTCTCTCTC ACAACCTGTG TAGAGCCCTC   120
CTGCCTGGAC ACTTGTGATG CGGCCCCAGC TCTCACTGCT ACTGGGTGTC CGATTTCTAG   180
AAAAAACCAA TCAGAGTCTC CGCGGTTCCC GGGTTTAAAG TCTCCACCGA CCCGCCCAAC   240
TCTGCTCCTT TCCAGACCCA GAGGACGCGA GTCATGGGGC CGCGAGCCCT CCTCCTGCTG   300
CTCTCGGGGG TCCTGATCCT GACTGAGACC CG                                332
```

( 2 ) INFORMATION FOR SEQ ID NO:2:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:2:

AGGCGTTGGC TCTCAGGGTC TCA                    23

(2) INFORMATION FOR SEQ ID NO:3:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:3:

CGGGTCTCAG TCAGGATCAG GA                     22